United States Patent [19]

Henkin et al.

[11] Patent Number: 5,323,783
[45] Date of Patent: Jun. 28, 1994

[54] DYNAMIC ST SEGMENT ESTIMATION AND ADJUSTMENT

[75] Inventors: Raphael Henkin, Monarch Beach, Calif.; George Kelen, Staten Island, N.Y.

[73] Assignee: Del Mar Avionics, Irvine, Calif.

[21] Appl. No.: 974,946

[22] Filed: Nov. 12, 1992

[51] Int. Cl.⁵ .......................................... A61B 5/0452
[52] U.S. Cl. .................................................. 128/703
[58] Field of Search ............................... 128/702, 703

[56] References Cited

U.S. PATENT DOCUMENTS

| | | | |
|---|---|---|---|
| 3,554,187 | 1/1971 | Glassner et al. | 128/703 |
| 3,606,882 | 9/1971 | Abe et al. | 128/704 |
| 4,124,894 | 11/1978 | Vick et al. | 128/703 |
| 4,622,980 | 11/1986 | Kunig | 128/704 |
| 4,924,875 | 5/1990 | Chamoun | 128/703 |
| 4,930,075 | 5/1990 | Kortas | 128/703 |
| 5,003,983 | 4/1991 | Dingwall et al. | 128/704 |
| 5,092,340 | 5/1992 | Yamaguchi et al. | 128/704 |

*Primary Examiner*—William E. Kamm
*Attorney, Agent, or Firm*—J. D. Leimbach

[57] ABSTRACT

A method and apparatus for dynamically estimating the ST segment of a rate varying electrocardiogram by comparing the result yielded from a mathematical relationship between calculated beat averages and a predetermined standard. Typically a table of known heartbeats is made from which means for estimating are created. An average of beat to beat intervals is compared with the means for estimating and the length of the ST segment for any particular beat is derived making it possible to dynamically alter ST segment length for any given heartrate.

20 Claims, 6 Drawing Sheets

DYNAMIC ST SEGMENT ESTIMATION AND ADJUSTMENT

BACKGROUND OF THE INVENTION

1. Field of the Invention

The present invention relates to analyzing electrocardiographic signals within stress testing systems, and more specifically, to estimating the length of ST segments within electrocardiographic signals as the rate at which the heart beats change as a result of exercise.

2. Description of the Prior Art

Numerous stress test systems exist that test electrocardiographic signals. These systems perform many functions that need to be performed within a stress test system including the construction of a digital representation of the ECG to be analyzed. Conventional stress test systems use a previously defined length for the ST segments in analysis of the digital representation of ECG signals. While this standard length gives some value for an ST segment, it does not provide a realistic estimate of the dynamically changing value of the ST segment. Changes that occur in the ST segment as a result of varying rates of heartbeats will go unnoticed without some method or apparatus for dynamically altering the ST segment to provide a realistic estimate of the length of the ST segment.

Is should be apparent from the foregoing discussion that there is a need for a system in which the ST segment is dynamically altered in response to varying rates of heartbeats. The present invention provides such a system.

SUMMARY OF THE INVENTION

A system is disclosed for estimating ST segments of electrocardiographs in stress test systems. The system requires that a digital representation of electrocardiographic signals be acquired from a human subject. From this digital representation the system calculates an average R to R interval within a predetermined period, usually 8 to 16 beats. The system has stored either a table of predetermined heartbeats or an equation that is derived from such a table by for example a least square fitting routine, that provides an estimated value for ST segments based on the calculated heart rate. By comparing the calculated average R to R interval with the predetermined set of varying heartbeats, an estimates ST value can be extracted from the predetermined set and be used as an estimated value on the digital representation of the electrocardiograph.

DESCRIPTION OF THE PREFERRED EMBODIMENT

A filtering method and apparatus has been discovered that is useful in correcting the length of ST segments within time varying electrocardiographic signals. The present invention is envisioned as being used within a stress test environment. However, it is also envisioned by the inventor that the generic properties of the present invention have uses beyond the stress testing environment disclosed, herein, as the preferred embodiment.

Figure 1:
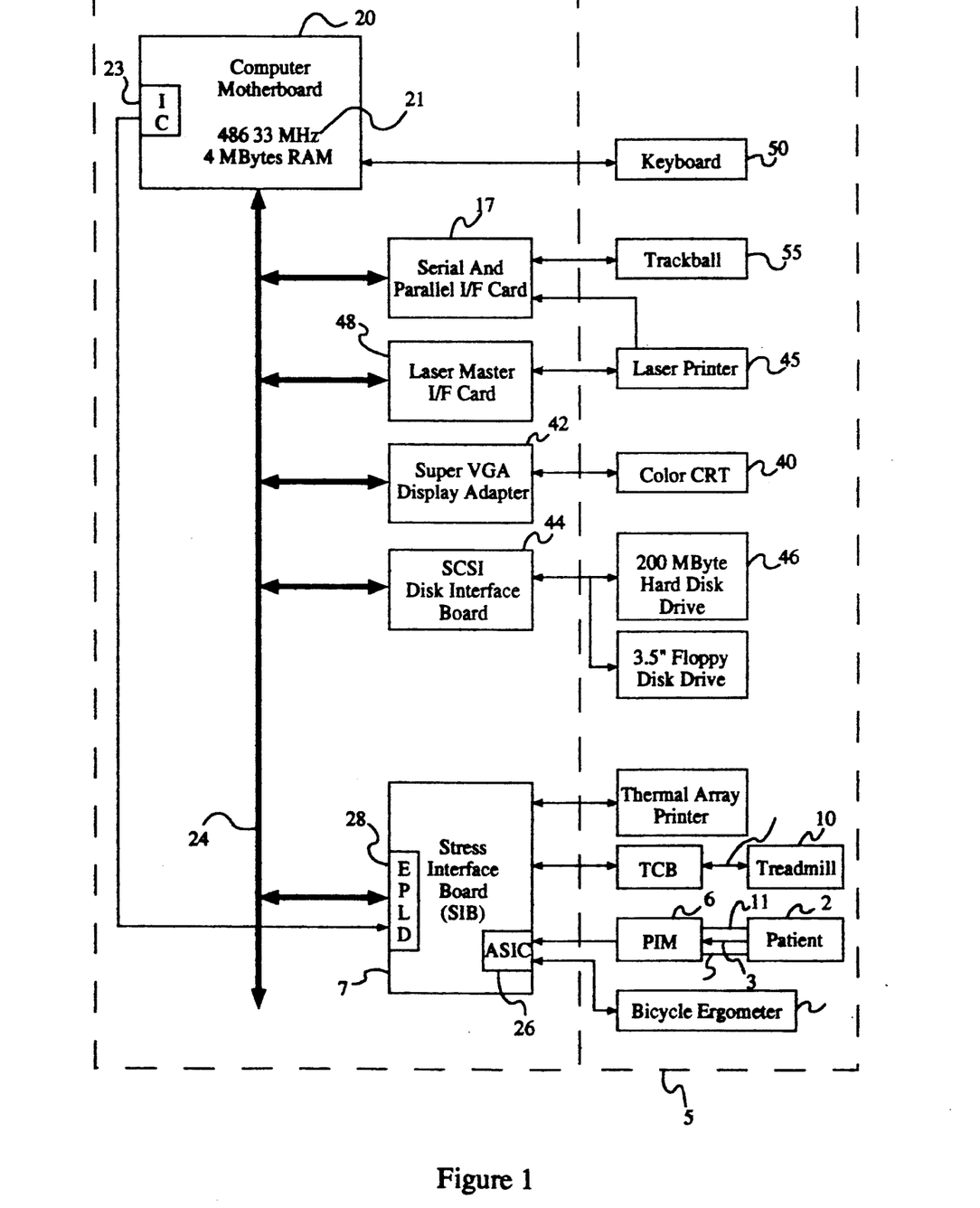
FIG. 1 is a block diagram for the Stress Test System.
Figure 2:
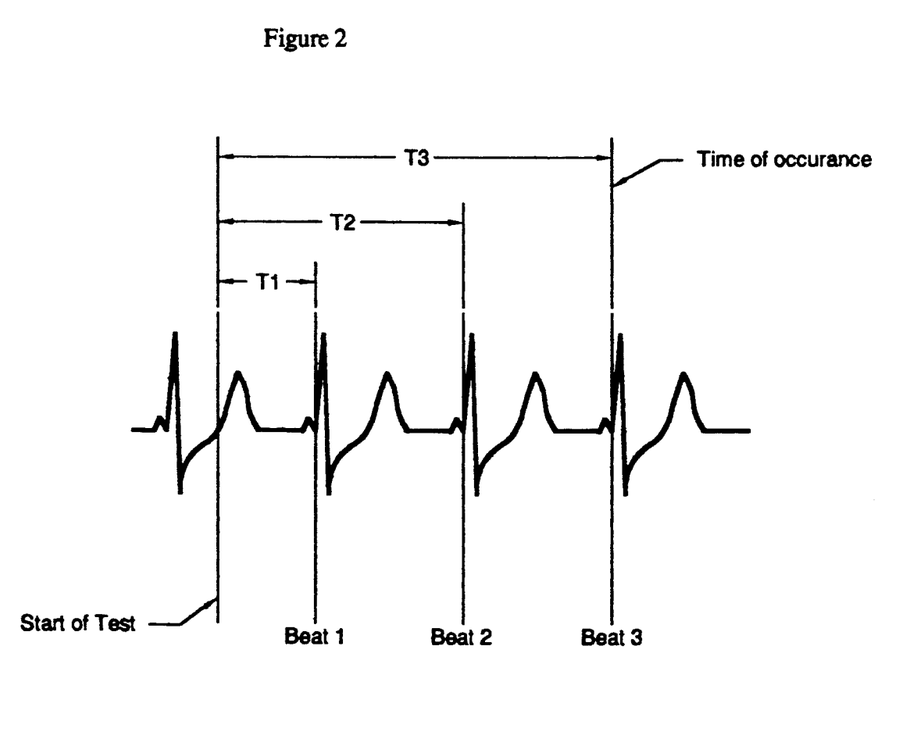
FIG. 2 is a diagram detailing the determination of the QRS Time of Occurrence.

Referring to FIG. 1, the basic stress test system 5 can be seen which requires some means for exercising the subject 2. The preferred embodiment employs treadmill 10 as a means for accelerating the heartbeat of subject 2. The subject 2 has a plurality of electrodes 3 attached which detect bioelectric signals of the heart of subject 2. Electrodes 3 generate analog ECG signals which are converted to digital signals by Patient Input Module (PIM) 6. PIM 6 is located close to subject 2 to avoid signal drop over a long conductor prior conversion to a digital format.

Serial data are output from PIM 6 to the computer 20 of the stress test system 5 through Stress Interface Board (SIB) 7 within computer 20 receives the serial data generated by PIM 6. The serial data are transmitted by PIM 6 along with clock, power and ground signals are transmitted by PIM 6 on separate conductors to SIB 20 where they these signals are used by the computer 20 of stress test system 5. The serial data are converted into a parallel format by SIB 7 which also synchronizes the parallel data with clock signals received by SIB 7. The serial data are converted into parallel data by ASIC device 26 which performs the function of a receiver gate array and takes the data and clock from the data/clock interface 22 and converts the serial data into 16 bit parallel words. These 16 bit parallel words are next sent to EPLD device 8 which is an interface circuit between the computer bus 24 and ASIC device 26. EPLD device will interface with the computer 19 to determine the exact times at which data is placed on computer bus 24. SIB 7 has an interface to the treadmill stress system via RS232 interface 34 which exchanges data with treadmill 10 via a serial interface. Patient data 32 within ASIC device 26, and treadmill 10 data are sent to the CPU 21 across computer bus 34 under interrupt control; by interrupt controller 23.

The remaining basic components of the stress test system consists of CRT 40, laser printer 45, a keyboard 50, trackball 55 and isolation transformer 60. Computer 20 interfaces with peripheral very commonly found within computer workstations. These peripherals are Generally operated under the control of CPU 21, consist of SCSI controller board 44, VGA display controller board 42, CRT 40, hard disc 46, laser printer interface board (hereinafter referred as the "Lasermaster") 48 Serial/Parallel interface board 17 and stress interface board (SIB) 7.

Referring now to FIG. 1, the system shall record each event and assign a time of occurrence that is measured from the time at which the event occurred as measured in milliseconds from the start of the test. The system detects QRS complexes by processing several ECG leads. For each QRS detected, the system shall determine the onset of the QRS and the classification label for the beat. Referring to FIG. 1, for each QRS detected, the system shall record: 1) the time of occurrence of the beat; 2) the previous R to R interval; 3) average RR interval and 4) beat classification label. Equation 1 below shows the method of calculation used for the previous R to R interval. The previous RR interval shall be determined for all beats detected except the first beat detected after the initiation of testing.

$$\text{Previous RR beat}_i = T_i - T_j - 1 \quad (1)$$

The system uses the values calculated for previous RR intervals to determine the average RR interval as shown in equation 2.

$$\frac{1}{8} \sum_{J=0}^{J=7} \text{Prev } RR_{i-j} \quad \text{Equation 2}$$

Beats are classified in to one of the following classes: 1 normal; 2) supraventricular premature beat; 3) premature ventricular contraction; 4) ventricular escape beat; 5) beat of unknown origin; and 6) not QRS.

Rhythm calculations consist of heart rate calculations and arrhythmia event detection are performed by the system as follows. The instantaneous heart rate (IHR) is determined for the previous RR interval as shown in equation 3.

$$IHR = \frac{60 \times 1000 \text{ milliseconds}}{\text{Previous } RR \text{ Beat}_i \text{ (in milliseconds)}} \quad \text{Equation 3.}$$

The system then uses the values calculated as previously detailed for average RR interval to calculate average heart rate as shown by equation 4.

$$AHR = \frac{60 \times 1000 \text{ milliseconds}}{\text{Average } RR \text{ beat}_i \text{ (in milliseconds)}} \quad \text{Equation 4.}$$

Analysis on the filtered data calculates and records information on a beat by beat basis. This information comprises time of occurrence of the beat, the R to R interval of previous beats and an average R to R interval. Beats are then given a classification label as being one of the following classes: (1) normal; (2) supraventricular premature beat (atrial or nodal); (3) premature ventricular contraction; (4) ventricular escape beat; (5) beat of unknown origin; or (6) not QRS. Rhythm/Event Calculation shall compute a value for instantaneous heart rate (IHR) as a function of the previous R to R interval and also calculate a value for average heart rate using the average R to R interval. Rhythm/Event Calculation will then detect and record the arrhythmia events as detailed in Table 1 below. For each of these events the system shall store the start time and the end time of the event.

TABLE 1

| Number | Event Name | Meaning |
|---|---|---|
| 1 | Couplet | Two consecutive ventricular exsystol (VE) beats |
| 2 | Triplet | Three consecutive VE beats |
| 3 | Pause | Two beats where the R to R interval is longer > 2 sec. |
| 4 | Bigeminy | xVxVxV pattern where V is a VE beat and x is not. |
| 5 | Trigeminy | xxVxxVxxV pattern where V is a VE beat and x is not. |
| 6 | Ventricular Tachycardia | Four or more consecutive VE beats. |
| 7 | Superventricular Tachycardia | Three or more consecutive beats intervals each 20% permature with a 3 beat avg. heat rate ≧ 80 bpm. |
| 8 | Bradycardia | Three or more consecutive beats at a rate lower than 45 bpm with the three most recent intervals greater than 1500 msec. |
| 9 | Average VE count per minute | A sliding window count of VE beats equal to 1 minute that is updated every second |

TABLE 1-continued

For each lead being analyzed in the system, the system shall perform average beat calculation. The average beat is a template of the QRS that is calculated by time aligning and averaging the previous 8 QRS complexes that meet certain criteria. When the system detects a QRS, it shall compare the candidate QRS to the currently stored template. If the candidate QRS is sufficiently similar in shape (as determined by certain criteria internal to the system), the candidate ARS is then used to update the current template. The average QRS shall be stored every 8th time the internal template is updated. The system shall perform the measurements described below on each of the stored average QRS complexes. For each average beat calculated, the system shall measure the following items on all leads being processed by the system: 1) ST level measurements; 2) ST slope measurements; 3) ST integral measurements; 4) ST index measurements; 5) QRS amplitude and duration measurements; 6) average RR interval; and 7) time of average beat calculation. Each of these will be described in more detail below.

Figure 3:
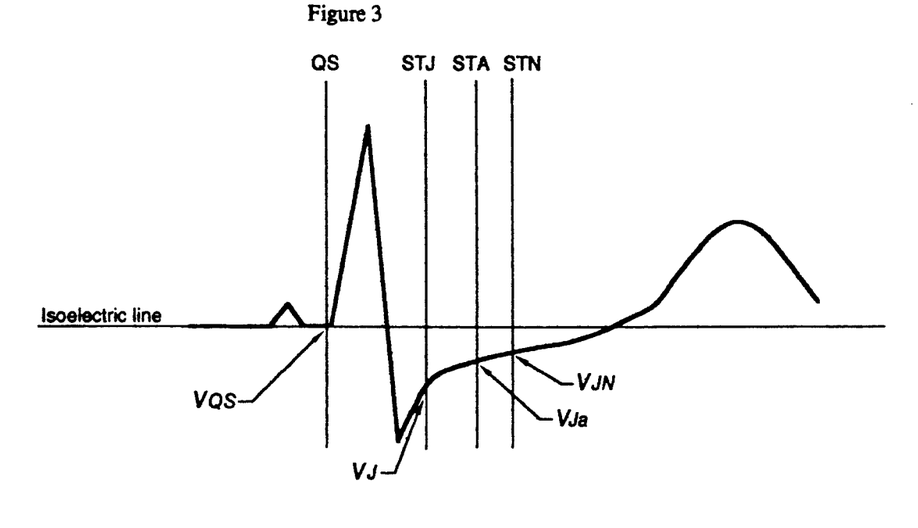
FIG. 3 is an illustration of the basic reference points used in ST measurements.

Referring to FIG. 3, which is an illustration of the basic reference points used for ST measurements, the ST and QRS measurements made on the QRS complexes are illustrated. The points labeled QS and J in FIG. 3 are dynamically determined from all currently active leads by the analysis software. The point labeled QS represents the start of the QRS complex while the point labeled J represents the termination of the QRS complex. The ST level is measured in volts at three different points within the ST segment. The voltage level as measured at J is indicated as STJ. A distance we shall call a from J is a delay determined from the average of the previous R to R intervals as described by equation 5, the point a milliseconds from J is referred to as STA. The value 'a' in Equation 5 is an estimation that is arrived at from a least squared fitting routine.

$$a = \frac{8}{3}((2ARR)^{\frac{1}{2}} - 16) \text{ in milliseconds} \quad \text{Equation 5}$$

The third voltage level measured along the ST segment is a point N milliseconds from the J point, that is determined by the operator. The voltage level at this point is referred to as STN.

A truly novel feature of the present invention is the ability to determine dynamically varying ST voltage levels. Table 2 lists the values for a as calculated for several different heart rates rounded to the nearest millisecond.

TABLE 2

| ST Measurements For Several Heartrates | | |
|---|---|---|
| Heart Rate (in BPM) | ARR Interval (in msec) | Value of "a" (in msec) |
| 60 | 1000 | 76 |
| 80 | 750 | 60 |
| 120 | 500 | 41 |
| 160 | 375 | 30 |
| 200 | 300 | 23 |

TABLE 2-continued

ST Measurements For Several Heartrates

| Heart Rate (in BPM) | ARR Interval (in msec) | Value of "a" (in msec) |
|---|---|---|
| 240 | 250 | 17 |

Table 3 illustrates the measurements made for ST level by the system. In addition to ST level, the system calculates the corrected ST level as indicated. The term QRSA is the amplitude of the QRS complex in millivolts divided by one millivolt, that serves as a correction factor for ECG signal strength. In addition to ST level and corrected ST level for each point, the system shall store the measurement points "a" and "N".

TABLE 3

ST Level Measurements

| Measurement Point | Measurement Point Determination | ST Level | Corrected ST |
|---|---|---|---|
| STJ | J + 0 msec. | $V_J - V_{QS}$ | $\dfrac{V_J - V_{QS}}{QRSA}$ |
| STJA | See Equation | $V_{STA} - V_{QS}$ | $\dfrac{V_{STA} - V_{QS}}{QRSA}$ |
| STJN | J + N msec. | $V_{STN} - V_{QS}$ | $\dfrac{V_{STN} - V_{QS}}{QRSA}$ |

Figure 4:
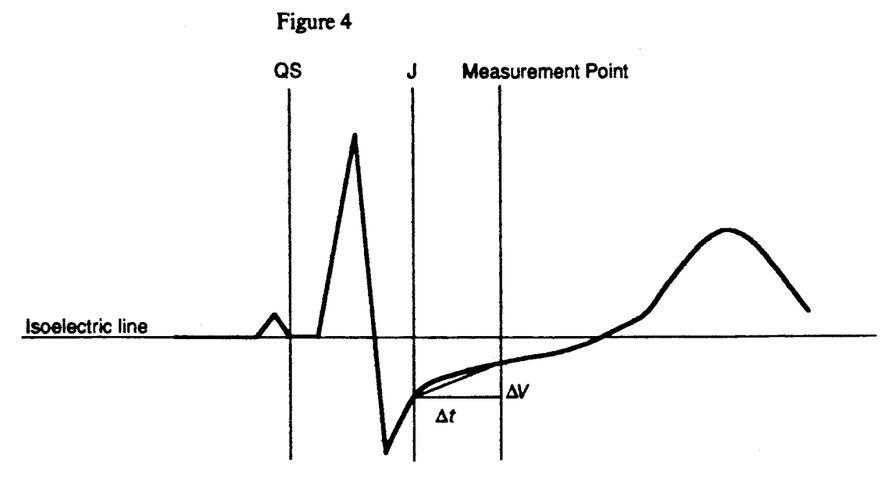
FIG. 4 is a diagram used for ST slope measurements.

Referring now to FIG. 4, an illustration of the method used to calculate the slope of the ST segment. There are two points of interest in calculating the slope of the ST segment. The first point is the J point. The voltage value (in millivolts) at the J point is then subtracted from the voltage value at the measurement point (MP). The difference is then divided by the distance between the two points (in seconds) to arrive at the slope. This relationship is shown by equation 6 below in which the ST slop is represented in millivolts per second.

$$\frac{V}{t} = \frac{V_{MP} - V_J (\text{in millivolts})}{MP - J (\text{in seconds})} \quad \text{Equation 6}$$

Figure 5:
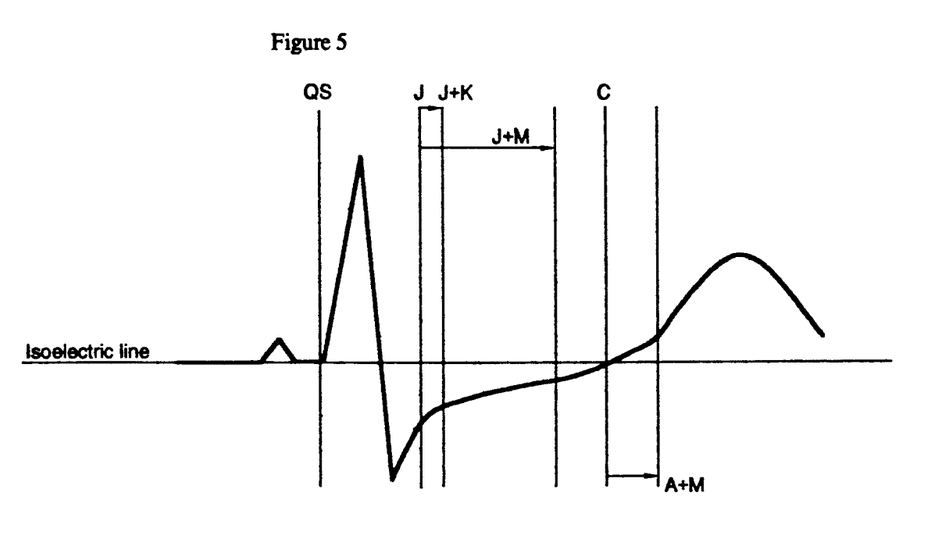
FIG. 5 is a diagram used to illustrate ST integral measurements.

Referring to FIG. 5, which is an illustration of the ST Integral measurement, the ST Integral is measured at three points. The first integral measurement occurs between the horizontal isoelectric line established at the onset of the QRS and the area enclosed by the ECG waveform between the J point and the point labeled C on FIG. 5 Point C is established as either the intersection between the ECG and the isoelectric line or as a predetermined amount of time after the J point if earlier than the intersection with the isoelectric line.

The second ST integral is measured between point J and the point "a" as established by equation 5 above.

The third measurement is predetermined point "N" which is a fixed value in milliseconds determined by the operator.

The ST integral is defined by equation 7 below.

$$ST \text{ Integral} = \sum_{i=J}^{i=C} (V_i - V_{QS}) \cdot \sigma t \text{ (in } \mu\text{volt} \cdot \text{seconds)} \quad \text{Equation 7}$$

The ST index is defined as the algebraic sum of the ST level in millimeters and the ST slope in millivolts per second. The system shall measure the ST index at two points as indicated in Table 4.

TABLE 4

ST Index Measurements

| Measurement Point | Calculation | Meaning |
|---|---|---|
| ST Index A | STA × 10 mm/mv + ST Slope A | ST Level at point A |
| ST Index N | STN × 10 mm/mv + ST Slope N | ST Level at point N |

Figure 6:
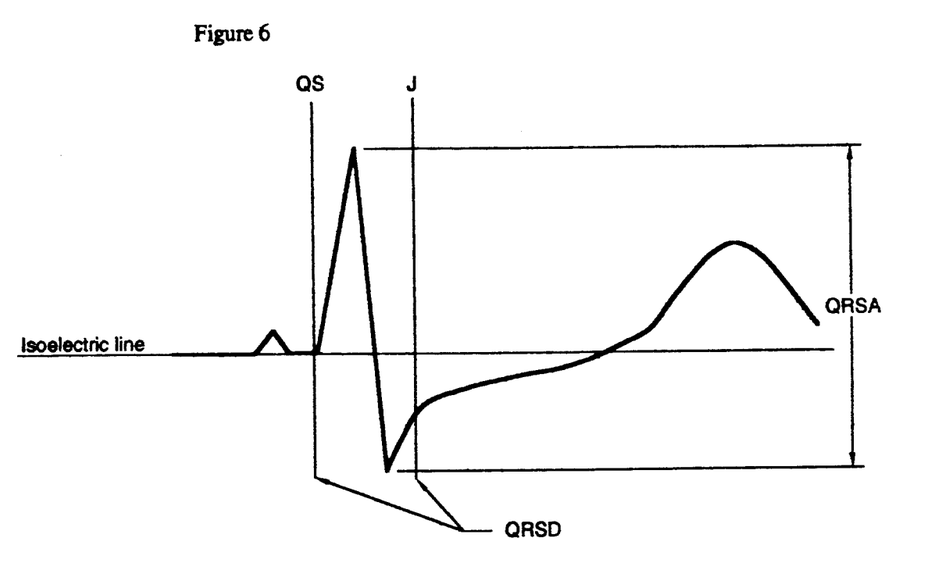
FIG. 6 is a diagram used to illustrate QRS Amplitude and Width Measurements.

Referring to FIG. 6, Average QRS Amplitude and Duration Measurements are performed by the system as indicated. Table 5 below illustrates the meaning for each the QRSA and the ARSD.

TABLE 5

ST QRS Measurements

| Measurement | UNITS | MEANING |
|---|---|---|
| QRSA | MILLIVOLTS | AMPLITUDE OF THE QRS |
| QRSD | MILLISECONDS | DURATION OF THE QRS COMPLEX |

The inventor envisions that the generic properties of the present invention have numerous applications and, while the best mode known to the inventor is disclosed in detail herein, sufficient disclosure is made to enable persons skilled within the arts of stress testing and digital signal processing to employ the invention towards other embodiments which are but obvious improvement over the disclosure of the present invention. These obvious variations would not, therefore, depart from the spirit and scope of the invention as defined in the appended claims.

What is claimed is:

1. A method for estimating ST segments of electrocardiographic signals comprising the steps of:
   acquiring a digital representation of electrocardiographic signals from a human subject;
   creating a predetermined set of varying heartrates, each of said set having a corresponding value for ST segments;
   detecting and measuring R to R intervals in said digital representation of electrocardiographic signals;
   calculating an R to R interval average from detected R to R intervals within said digital electrocardiographic signals;
   comparing said R to R interval average with said predetermined set of varying heartrates to determine which heartrate of said predetermined set equals said average R to R interval; and
   selecting from said predetermined heartrate said corresponding value for ST segment and using said corresponding value for an estimation of ST segment.

2. The process of claim 1 wherein said step of creating said predetermined set of varying heartrates further comprises applying a least square fitting routine to said predetermined set of varying heartrates to generate estimation means for estimating ST segments, and said comparing step applies said R to R interval average to said estimation means to arrive at an approximation for ST segment values.

3. The invention of claim 1 further comprising the step of modifying said digital representation to include as its ST segment said corresponding value.

4. The invention of claim 1 wherein said step of creating further comprises generating from said set estimation means for approximating ST segments of electrocardiographic signals, and said selecting step comprises incorporating ST segments approximated by said estimation means into said digital representation of electrocardiographic signals.

5. A stress test system for dynamically changing ST segment length in ECG signals in response to varying heart rates induced by exercise comprising:

exercise means for accelerating a subject's heart rate;

ECG acquisition means for obtaining a digital representation of said subjects electrocardiographic signal;

computational means for measuring and detecting QRS signals within said digital representation;

estimation means derived from a predetermined set of varying heartrates for generating an estimate of ST segment values for detected QRS signals measured within said digital representation;

comparison means for comparing measured QRS signals within said digital representation to said estimation means to determine an approximate ST segment length to be used as said estimated ST segment length; and means responsive to said comparison means for adjusting ST segment length within said digital representation to conform to said estimated ST length.

6. The invention of claim 5 wherein said estimation means comprises a least square fitting routine derived from said predetermined set of varied heartrates.

7. The invention of claim 5 wherein said estimation means comprises a table containing a set of heartrates, each member of said set containing an ST portion from which an ST segment can be selected.

8. The invention of claim 5 wherein said estimation means derived from a predetermined set of varying heartrates comprises an approximation determined by the relationship $$a = \frac{8}{3} ((2ARR)^{\frac{1}{2}} - 16) \text{ in milliseconds}$$

where
(1) a is said approximation of ST segments; and
(2) 2ARR is twice the average heartrate.

9. The invention of claim 5 further including adjustment means contained within said computational means to use said estimated ST segment as an ST segment of said digital representation.

10. A method for estimating ST segments of electrocardiographic signals comprising the steps of:

acquiring a digital representation of electrocardiographic signals from a human subject;

creating estimation means for estimating ST segments from a given heartrate;

calculating a heartrate interval from said digital electrocardiographic signals;

comparing said heartrate interval with said estimation means to determine values to be used as an estimated ST segment; and synthesizing said digital representation to reflect said estimated ST segment.

11. The method of claim 10 further comprising:

creating said estimation means from a least square fitting routine applied to a database of ST segment values for a predetermined set of various R to R intervals; and comparing said heartrate interval with said least squared fitting routine applied to said database of ST segment values for said predetermined set of various R to R intervals.

12. The method of claim 10 wherein said step of creating estimation means further comprises generating an equation from a least square fitting routine that estimates results from a table of preselected heartrates; and said comparing step further comprises inserting said heartrate interval into said equation to determine said estimated ST segment.

13. The method of claim 10 wherein said step of creating estimation means includes generating a table of varying heartrates, said table including a value for ST segments for each member of said set.

14. The method of claim 10 wherein said step of synthesizing said digital representation further includes adjusting said digital representation to include as its ST segment that of said estimated ST segment.

15. The method of claim 10 further including the step of repeating the steps of acquiring, creating, calculating, comparing and synthesizing, thereby, adjusting detected ECG signals on an iterative basis.

16. The method of claim 15 wherein said step of repeating further comprises basing said iterative basis on a periodical average of heartbeats.

17. A product for stress test systems made from the process defined by the steps of:

acquiring a digital representation of electrocardiography signals from a human subject, said digital representation of electrocardiographic signals being from an accelerated heart;

creating a predetermined set of varying heartrates, each of said set having a corresponding value for ST segments;

detecting and measuring R to R intervals in said digital representation of electrocardiographic signals;

calculating an R to R interval average from detected R to R intervals within said digital electrocardiographic signals;

comparing said R to R interval average with said predetermined set of varying heartrates to determine which heartrate of said predetermined set equals said average R to R interval; and selecting from said predetermined heartrate said corresponding value for ST segment and using said corresponding value for an estimation of ST segment.

18. The product as defined in claim 17 further defined by the process step of using as said predetermined set of varying heartbeats a function related to a set of predetermined heartbeats that estimates ST segments based on a given heartrate.

19. The product as defined in claim 18 further defined by the process step of using said function within said comparing step to compare said R to R interval with said function to estimate the location of ST segments.

20. The product as defined by claim 19 further defined by the process step of employing as said function an equation derived from a least square fitting routine from said predetermined set of varying heartrates.

* * * * *